(12) United States Patent
Tsuda

(10) Patent No.: US 11,167,259 B2
(45) Date of Patent: Nov. 9, 2021

(54) FLUORINATED CARBONATE DERIVATIVE PRODUCTION METHOD

(71) Applicants: NATIONAL UNIVERSITY CORPORATION KOBE UNIVERSITY, Kobe (JP); AGC Inc., Chiyoda-ku (JP)

(72) Inventor: Akihiko Tsuda, Kobe (JP)

(73) Assignees: NATIONAL UNIVERSITY CORPORATION KOBE UNIVERSITY, Kobe (JP); AGC Inc., Chiyoda-ku (JP)

( * ) Notice: Subject to any disclaimer, the term of this patent is extended or adjusted under 35 U.S.C. 154(b) by 147 days.

(21) Appl. No.: 16/605,635

(22) PCT Filed: Apr. 27, 2018

(86) PCT No.: PCT/JP2018/017349
§ 371 (c)(1),
(2) Date: Oct. 16, 2019

(87) PCT Pub. No.: WO2018/211953
PCT Pub. Date: Nov. 22, 2018

(65) Prior Publication Data
US 2020/0122114 A1 Apr. 23, 2020

(30) Foreign Application Priority Data

May 16, 2017 (JP) .............................. JP2017-097682

(51) Int. Cl.
| | | |
|---|---|---|
| *C08F 2/46* | (2006.01) | |
| *C08F 2/50* | (2006.01) | |
| *C08G 61/04* | (2006.01) | |
| *B01J 19/12* | (2006.01) | |
| *C07C 69/96* | (2006.01) | |
| *C08G 64/02* | (2006.01) | |
| *C08G 64/10* | (2006.01) | |
| *C08G 64/38* | (2006.01) | |
| *C08G 71/02* | (2006.01) | |
| *C08G 71/04* | (2006.01) | |

(52) U.S. Cl.
CPC ............ *B01J 19/123* (2013.01); *C07C 69/96* (2013.01); *C08G 64/0233* (2013.01); *C08G 64/10* (2013.01); *C08G 64/38* (2013.01); *C08G 71/02* (2013.01); *C08G 71/04* (2013.01); *B01J 2219/0884* (2013.01); *B01J 2219/1203* (2013.01)

(58) Field of Classification Search
CPC ... C07C 68/00; C07C 69/96; C07C 273/1809; C07C 275/30; B01J 19/123; B01J 2219/1203; B01J 2219/0884; C08G 64/0233; C08G 64/305; C08G 64/30; C08G 64/10; C08G 64/38; C08G 64/208; C08G 71/02; C08G 71/04
USPC .................................................... 522/1; 520/1
See application file for complete search history.

(56) References Cited

U.S. PATENT DOCUMENTS

| | | | |
|---|---|---|---|
| 5,728,773 A | 3/1998 | Jing et al. | |
| 5,929,169 A | 7/1999 | Jing et al. | |
| 2006/0135662 A1* | 6/2006 | Mullen ................... | C08L 69/00 524/157 |

FOREIGN PATENT DOCUMENTS

| | | | |
|---|---|---|---|
| JP | 10-77339 | A | 3/1998 |
| JP | 10-291965 | A | 11/1998 |
| JP | 11-152328 | A | 6/1999 |
| JP | 2000-319230 | | * 11/2000 |
| JP | 2000-319230 | A | 11/2000 |
| JP | 2001-512515 | A | 8/2001 |
| JP | 2013-181028 | | * 9/2013 |
| JP | 2013-181028 | A | 9/2013 |

OTHER PUBLICATIONS

Mori, JP 2000-319230 Machine Translation Nov. 21, 2000 (Year: 2000).*
Tsuda, JP 2013-181028 Machine Translation, Sep. 12, 2013 (Year: 2013).*
Extended European Search Report dated Nov. 19, 2020 in European Patent Application No. 18801749.5, 9 pages.
Schoorl: "RX-ID 6330183" Chemisches Zentralblatt, vol. 76, No. II, XP055747195, Jan. 1, 1905, p. 1623.

(Continued)

*Primary Examiner* — Jessica Whiteley
(74) *Attorney, Agent, or Firm* — Oblon, McClelland, Maier & Neustadt, L.L.P.

(57) ABSTRACT

The objective of the present invention is to provide a method for producing a fluorinated carbonate derivative in a safe and efficient manner. The method for producing a fluorinated carbonate derivative according to the present invention is characterized in comprising irradiating light on a composition containing a $C_{1-4}$ halogenated hydrocarbon having one or more kinds of halogen atoms selected from the group consisting of a chlorine atom, a bromine atom and an iodine atom, a fluorine-containing compound having a nucleophilic functional group and a base in the presence of oxygen.

12 Claims, 1 Drawing Sheet

(56) References Cited

OTHER PUBLICATIONS

International Search Report dated Jul. 10, 2018 in PCT/JP2018/017349 filed Apr. 27, 2018.
Kuwahara, Y. et al., "Photochemical Molecular Storage of $Cl_2$, HCl, and $COCl_2$: Synthesis of Organochlorine Compounds, Salts, Ureas, and Polycarbonate with Photodecomposed Chloroform," Organic Letters, vol. 14, No. 13, 2012, pp. 3376-3379.
Office Action as received in the corresponding EP patent application No. 18801749.5 dated Jul. 7, 2021, 4 pages.

* cited by examiner

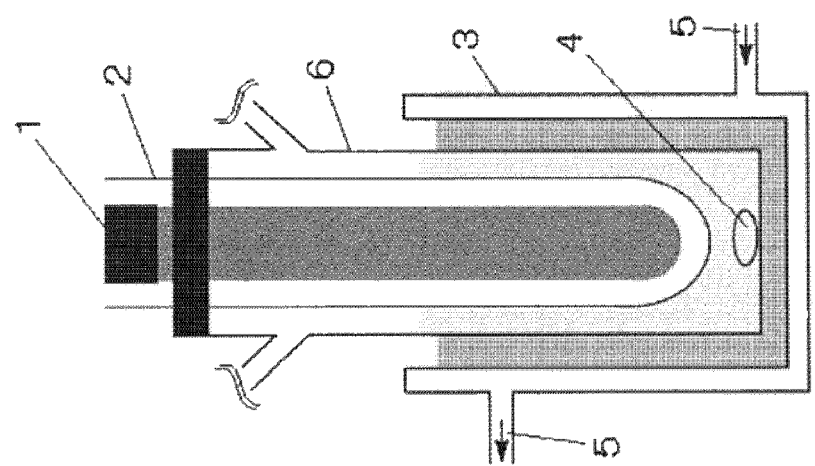

FLUORINATED CARBONATE DERIVATIVE PRODUCTION METHOD

TECHNICAL FIELD

The present invention relates to a method for producing a fluorinated carbonate derivative in a safe and efficient manner.

BACKGROUND ART

A fluorinated carbonate derivative is used in various applications, since the carbonate has a unique physical property. For example, the fluorinated carbonate represented by the following formula ($I^1$) is used for an electrolyte solution of a lithium ion secondary battery as a fire retardant solvent having a high flash point. The fluorinated polycarbonate containing a unit represented by the following formula ($I^2$) is used as an engineering plastic excellent in transparency and impact resistance.

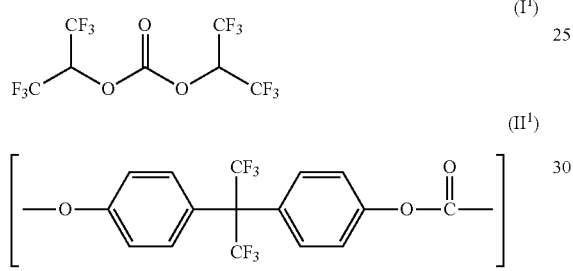

As a method for producing a fluorinated carbonate derivative, a method to react phosgene with a fluorine-containing compound having a nucleophilic functional group, a method to react carbon monoxide with the aforesaid fluorine-containing compound, and a method to transesterify a separately produced carbonate by the aforesaid fluorine-containing compound are known. The methods, however, are not a safe and efficient method for producing a fluorinated carbonate derivative, since it is needed to use phosgene or carbon monoxide, which are difficult to be handled, or a carbonate must be separately prepared.

On the one hand, the present inventor has developed a method for producing a halogenated formate ester which method contains the steps of obtaining a mixture of phosgene by irradiating light on chloroform in the presence of oxygen and reacting an alcohol with the mixture without isolating the phosgene (Patent document 1).

PRIOR ART DOCUMENT

Patent Document

Patent document 1: JP 2013-181028 A

DISCLOSURE OF THE INVENTION

Problems to be Solved by the Invention

The objective of the present invention is to provide a method for producing a fluorinated carbonate derivative in a safe and efficient manner.

Means for Solving the Problems

The inventor of the present invention made extensive studies. As a result, the inventor completed the present invention by finding that a fluorinated carbonate derivative can be produced with high yield in a safe and efficient manner by irradiating light on a composition containing a halogenated hydrocarbon, a fluorine-containing compound having a nucleophilic functional group and a base in the presence of oxygen.

Hereinafter, the present invention is described.

[1] A method for producing a fluorinated carbonate derivative, comprising irradiating light on a composition containing a $C_{1-4}$ halogenated hydrocarbon having one or more kinds of halogen atoms selected from the group consisting of a chlorine atom, a bromine atom and an iodine atom, a fluorine-containing compound having a nucleophilic functional group and a base in the presence of oxygen, wherein the fluorine-containing compound is a compound represented by the following formula (i) and the fluorinated carbonate derivative is a fluorinated carbonate derivative represented by the following formula (I), or the fluorine-containing compound is a compound represented by the following formula (ii) and the fluorinated carbonate derivative is a fluorinated polycarbonate derivative containing a unit represented by the following formula (II-1) or a fluorinated cyclic carbonate derivative represented by the following formula (II-2).

$$R^{F1}\text{-A-H} \qquad (i)$$

$$H\text{-A-}R^{F2}\text{-A-H} \qquad (ii)$$

$$R^{F1}\text{-A-C}(=O)\text{-A-}R^{F1} \qquad (I)$$

$$[\text{-A-}R^{F2}\text{-A-C}(=O)\text{—}] \qquad (II\text{-}1)$$

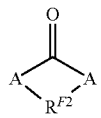

(II-2)

wherein
A is O, S or NH,
$R^{F1}$ is an unreactive fluorine atom-containing monovalent organic group,
$R^{F2}$ is an unreactive fluorine atom-containing divalent organic group.

[2] The production method according to the above [1], wherein the fluorine-containing compound is a compound represented by the following formula (i-1) and the fluorinated carbonate derivative is a fluorinated carbonate derivative represented by the following formula (I-1), the fluorine-containing compound is a compound represented by the following formula (i-2) and the fluorinated carbonate derivative is a fluorinated carbonate derivative represented by the following formula (I-2), or the fluorine-containing compound is a compound represented by the following formula (i-3) and the fluorinated carbonate derivative is a fluorinated carbonate derivative represented by the following formula (I-3).

$$R^{F11}CH_2\text{-A-H} \qquad (i\text{-}1)$$

$$(R^{F12})_2CH\text{-A-H} \qquad (i\text{-}2)$$

$(R^{F13})_3$-C-A-H (i-3)

$R^{F11}CH_2$-A-C(=O)-A-$CH_2$—$R^{F11}$ (I-1)

$(R^{12})_2$CH-A-C(=O)-A-CH$(R^{F12})_2$ (I-2)

$(R^{F13})_3$C-A-C(=O)-A-C$(R^{F13})_3$ (I-3)

wherein

A means the same as defined above, $R^{F11}$ is a $C_{1-10}$ fluoroalkyl group, a $C_{6-14}$ fluoroaryl group, a $C_{4-14}$ fluoroheteroaryl group or a $C_{2-24}$ fluoro(alkylpolyoxyalkylene) group, two $R^{F12}$ are independently a $C_{1-10}$ alkyl group, a $C_{1-10}$ fluoroalkyl group, a $C_{6-14}$ aryl group, a $C_{6-14}$ fluoroaryl group, a $C_{4-14}$ heteroaryl group, a $C_{4-14}$ fluoroheteroaryl group, a $C_{2-24}$ alkylpolyoxyalkylene group or a $C_{2-24}$ fluoro(alkylpolyoxyalkylene) group, and one or two $R^{F12}$ are a $C_{1-10}$ fluoroalkyl group, a $C_{6-14}$ fluoroaryl group, a $C_{4-14}$ fluoroheteroaryl group or a $C_{2-24}$ fluoro(alkylpolyoxyalkylene) group, or two $R^{F12}$ cooperatively form a $C_{2-6}$ fluoroalkylene group or a 1,2-fluoroarylene group, three $R^{F13}$ are independently a $C_{1-10}$ alkyl group, a $C_{1-10}$ fluoroalkyl group, a $C_{6-14}$ aryl group, a $C_{6-14}$ fluoroaryl group, a $C_{4-14}$ heteroaryl group, a $C_{4-14}$ fluoroheteroaryl group, a $C_{2-24}$ alkylpolyoxyalkylene group or a $C_{2-24}$ fluoro(alkylpolyoxyalkylene) group, and one, two or three $R^{F13}$ are a $C_{1-10}$ fluoroalkyl group, a $C_{6-14}$ fluoroaryl group, a $C_{4-14}$ fluoroheteroaryl group or a $C_{2-24}$ fluoro(alkylpolyoxyalkylene) group.

[3] The production method according to the above [1], wherein the fluorine-containing compound is a compound represented by the following formula (ii-1) and the fluorinated carbonate derivative is a fluorinated polycarbonate derivative represented by the following formula (II-11), or the fluorine-containing compound is a compound represented by the following formula (ii-2) and the fluorinated carbonate derivative is a fluorinated cyclic carbonate derivative represented by the following formula (II-21) or a fluorinated linear carbonate derivative represented by the following formula (II-22).

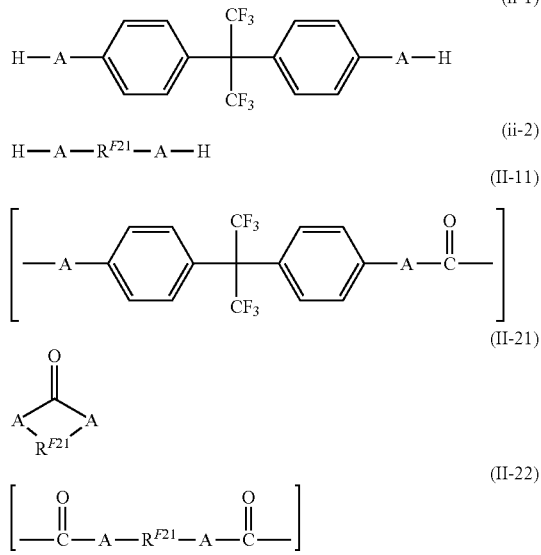

wherein

A means the same as defined above, $R^{F21}$ is a $C_{3-10}$ fluoroalkylene group or a poly($C_{1-4}$ fluoroalkyleneoxy) group.

[4] The production method according to any one of the above [1] to [3], wherein the $C_{1-4}$ halogenated hydrocarbon is a $C_{1-4}$ polyhalogenated hydrocarbon.

[5] The production method according to any one of the above [1] to [3], wherein the $C_{1-4}$ halogenated hydrocarbon is chloroform.

[6] The production method according to any one of claims 1 to 5, wherein the base is one or more bases selected from the group essentially consisting of a heterocyclic aromatic amine, a non-nucleophilic strong base and an inorganic base.

[7] The production method according to the above [6], wherein the heterocyclic aromatic amine is pyridine, picoline or lutidine.

[8] The production method according to the above [6], wherein the non-nucleophilic strong base is 1,5,7-triazabicyclo[4.4.0]dec-5-ene, 7-methyl-1,5,7-triazabicyclo[4.4.0]dec-5-ene, 1,8-diazabicyclo[5.4.0]undec-7-ene, 1,5-diazabicyclo[4.3.0]non-5-ene or 1,1,3,3-tetramethylguanidine.

[9] The production method according to the above [6], wherein the inorganic base is an alkali metal hydroxide, an alkali metal hydrogen carbonate or an alkali metal carbonate.

[10] The production method according to any one of the above [1] to [9], wherein 0.001 times or more by mole and 1 time or less by mole of the fluorine-containing compound is used to the $C_{1-4}$ halogenated hydrocarbon.

[11] The production method according to any one of the above [1] to [10], wherein 1.5 times or more by mole and 10 times or less by mole of the base is used to the fluorine-containing compound.

[12] The production method according to any one of the above [1] to [11], wherein a wavelength of the light irradiated on the composition is 180 nm or more and 500 nm or less.

Effect of the Invention

It is not needed in the present invention method that a compound which is difficult to be handled, such as phosgene and carbon monoxide, is used as a raw material compound. In addition, a transesterification reaction is not used. Thus, a fluorinated carbonate derivative can be produced in a safe and efficient manner by the present invention.

BRIEF DESCRIPTION OF THE DRAWINGS

FIG. 1 is a schematic picture to demonstrate an example of a reaction device usable in the present invention method.

MODE FOR CARRYING OUT THE INVENTION

In this disclosure, an alkyl group having 1 or more and 8 or less carbons is also described as a "$C_{1-8}$ alkyl group", and a halogenated hydrocarbon having 1 or more and 4 or less carbons is also described as a "$C_{1-4}$ halogenated hydrocarbon". The other group and the other compound are similarly described.

In the production method according to the present invention, a fluorinated carbonate derivative can be obtained in a safe and efficient manner by irradiating light on a composition containing a $C_{1-4}$ halogenated hydrocarbon having one or more kinds of halogen atoms selected from the group consisting of a chlorine atom, a bromine atom and an iodine atom, a fluorine-containing compound having a nucleophilic functional group and a base in the presence of oxygen.

The reason is not necessarily clear but the inventor considers as follows. The nucleophilic functional group of the fluorine-containing compound in the composition according to the present invention is considered to be in a highly active state by an interaction with the base, since an acidity of the nucleophilic functional group of the fluorine-containing compound is high. Thus, a halogenated carbonyl or a halogenated carbonyl-like compound generated from the $C_{1-4}$ halogenated hydrocarbon by an irradiation of light in the presence of oxygen may be immediately reacted with the nucleophilic functional group of the fluorine-containing compound to form the fluorinated carbonate derivative. In other words, the base not only captures a hydrogen halide generated as a by-product in association with a formation of the fluorinated carbonate derivative but also has a function to activate the nucleophilic functional group of the fluorine-containing compound in the production method of the present invention. As a result, since a halogenated carbonyl-like compound is reacted with the fluorine-containing compound immediately after the generation, the fluorinated carbonate derivative can be produced in a safe and efficient manner by the production method of the present invention. On the one hand, a halogenated carbonyl compound may not possibly mediate the reaction of the present invention, since the reaction of the present invention proceeds in the presence of an inorganic base aqueous solution as described later.

The $C_{1-4}$ halogenated hydrocarbon usable in the present invention may be decomposed due to the irradiated light and oxygen into a halogenated carbonyl compound such as a halogenated carbonyl and reacted with the fluorine-containing compound having the nucleophilic functional group to generate the fluorinated carbonate derivative. Discharge of a halogenated carbonyl-like compound can be controlled without difficulty in the production method of the present invention, since the halogenated carbonyl compound is immediately reacted with the fluorine-containing compound having the nucleophilic functional group which is activated by the base.

A $C_{1-4}$ polyhalogenated hydrocarbon is preferred as the $C_{1-4}$ halogenated hydrocarbon from the viewpoint that a halogenated carbonyl compound can be easily generated. The $C_{1-4}$ polyhalogenated hydrocarbon means a compound corresponding to a $C_{1-4}$ hydrocarbon of which two or more hydrogen atoms are substituted with a halogen atom. The $C_{1-4}$ halogenated hydrocarbon is preferably substituted with one kind or two or more kinds of halogen atoms, more preferably one kind of a halogen atom, and particularly preferably a chlorine atom only.

As the $C_{1-4}$ halogenated hydrocarbon, a $C_{1-4}$ halogenated alkane, a $C_{2-4}$ halogenated alkene or a $C_{2-4}$ halogenated alkyne is preferred, a halogenated methane, a halogenated ethene or a halogenated acetylene is more preferred in terms of an easy generation of a halogenated carbonyl-like compound, a polyhalogenated methane, a polyhalogenated ethene or a polyhalogenated acetylene is particularly preferred, a polyhalogenated methane is more preferred, and chloroform is the most preferred.

A specific example of the $C_{1-4}$ halogenated hydrocarbon includes a halogenated methane such as dichloromethane, chloroform, tetrachloromethane, dibromomethane, bromoform, tetrabromomethane, iodomethane, diiodomethane and tetraiodomethane; a halogenated ethane such as 1,1,2-trichloroethane, 1,1,1-trichloroethane, 1,1,2,2-tetrachloroethane, 1,1,1,2-tetrachloroethane, hexachloroethane and hexabromoethane; and a halogenated propane such as 1,1,1,3-tetrachloropropane.

One kind of the $C_{1-4}$ halogenated hydrocarbon may be singly used, and alternatively two or more kinds of the $C_{1-4}$ halogenated hydrocarbons may be used in combination, and it is preferred to use one kind singly.

The $C_{1-4}$ halogenated hydrocarbon may be a recovered $C_{1-4}$ halogenated hydrocarbon which has been once used as a solvent. It is preferred that such a recovered $C_{1-4}$ halogenated hydrocarbon is purified, since an impurity and water is contained and thus the reaction may be possibly inhibited. An example of a purification means includes a method in which a water-soluble impurity is removed by washing the recovered $C_{1-4}$ halogenated hydrocarbon with water, an aqueous phase and an organic phase are separated, and the organic phase is dehydrated by using a dehydrating agent such as anhydrous sodium sulfate and anhydrous magnesium sulfate.

An excessive purification by which the productivity becomes less is not needed, since the water contained in the recovered $C_{1-4}$ halogenated hydrocarbon may not inhibit the reaction. The water content in the recovered $C_{1-4}$ halogenated hydrocarbon is preferably 0.5 vol % or less, more preferably 0.2 vol % or less, and particularly preferably 0.1 vol % or less. The recovered $C_{1-4}$ halogenated hydrocarbon may contain a degradant of the $C_{1-4}$ halogenated hydrocarbon.

The "nucleophilic functional group" in the present invention means a nucleophilic functional group which has a nucleophilic oxygen atom, sulfur atom and/or nitrogen atom. The fluorine-containing compound having the nucleophilic functional group usable in the present invention is a compound represented by the following formula (i) or a compound represented by the formula (ii), and is also described as the "compound (i)" or the "compound (ii)". When the compound (i) is used, the obtained fluorinated carbonate derivative is the fluorinated carbonate derivative represented by the formula (I), which is abbreviated as the "compound (I)" in some cases. When the compound (ii) is used, the obtained fluorinated carbonate derivative is the fluorinated polycarbonate derivative containing the unit represented by the formula (II-1), which is abbreviated as the "polymer (II-1)", or the fluorinated cyclic carbonate derivative represented by the formula (II-2), which is abbreviated as the "compound (II-2)".

$$R^{F1}\text{-A-H} \tag{i}$$

$$\text{H-A-}R^{F2}\text{-A-H} \tag{ii}$$

$$R^{F1}\text{-A-C(=O)-A-}R^{F1} \tag{I}$$

$$[\text{-A-}R^{F2}\text{-A-C(=O)-}] \tag{II-1}$$

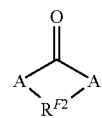

(II-2)

In the above formulae, "A" is O, S or NH, $R^{F1}$ is an unreactive monovalent fluorine atom-containing organic group, $R^{F2}$ is an unreactive divalent fluorine atom-containing organic group.

The above-described monovalent organic group is not particularly restricted as long as the monovalent organic group has a fluorine atom and is inactive against the reaction of the composition by the light irradiation in the presence of oxygen. The above-described divalent organic group is similarly not particularly restricted as long as the divalent organic group has a fluorine atom and is inactive against the reaction of the composition by the light irradiation in the presence of oxygen.

The compound (i) is preferably the compound represented by the following formula (i-1), the compound represented by the following formula (i-2) and the compound represented by the following formula (i-3) from the viewpoint that an acidity of the compounds are higher and the target compound can be efficiently obtained by activating the compounds with the base more efficiently, and the obtained compound (I) is preferably the compound represented by the following formula (I-1), the compound represented by the following formula (I-2) and the compound represented by the following formula (I-3) in this order.

(i-1)

(i-2)

(i-3)

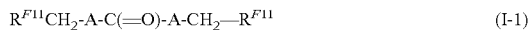

(I-1)

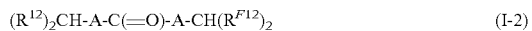

(I-2)

(I-3)

wherein "A" means the same as defined above, $R^{F11}$ is a $C_{1-10}$ fluoroalkyl group, a $C_{6-14}$ fluoroaryl group, a $C_{4-14}$ fluoroheteroaryl group or a $C_{2-24}$ fluoro(alkylpolyoxyalkylene) group.

The two $R^{F12}$ are independently a $C_{1-10}$ alkyl group, a $C_{1-10}$ fluoroalkyl group, a $C_{6-14}$ aryl group, a $C_{6-14}$ fluoroaryl group, a $C_{4-14}$ heteroaryl group, a $C_{4-14}$ fluoroheteroaryl group, a $C_{2-24}$ alkylpolyoxyalkylene group or a $C_{2-24}$ fluoro(alkylpolyoxyalkylene) group, and one or two $R^{F12}$ are a $C_{1-10}$ fluoroalkyl group, a $C_{6-14}$ fluoroaryl group, a $C_{4-14}$ fluoroheteroaryl group or a $C_{2-24}$ fluoro(alkylpolyoxyalkylene) group, or two $R^{F12}$ cooperatively form a $C_{2-6}$ fluoroalkylene group or a 1,2-fluoroarylene group.

The three $R^{F13}$ are independently a $C_{1-10}$ alkyl group, a $C_{1-10}$ fluoroalkyl group, a $C_{6-14}$ aryl group, a $C_{6-14}$ fluoroaryl group, a $C_{4-14}$ heteroaryl group, a $C_{4-14}$ fluoroheteroaryl group, a $C_{2-24}$ alkylpolyoxyalkylene group or a $C_{2-24}$ fluoro(alkylpolyoxyalkylene) group, and one, two or three $R^{F13}$ are a $C_{1-10}$ fluoroalkyl group, a $C_{6-14}$ fluoroaryl group, a $C_{4-14}$ fluoroheteroaryl group or a $C_{2-24}$ fluoro(alkylpolyoxyalkylene) group.

The $C_{1-10}$ alkyl group may be linear, branched or cyclic. The $C_{1-10}$ alkyl group is preferably a $C_{1-6}$ alkyl group and more preferably a $C_{1-4}$ alkyl group.

The $C_{1-10}$ fluoroalkyl group means a $C_{1-10}$ alkyl group of which one or more hydrogen atoms are substituted by a fluorine atom. The $C_{1-10}$ fluoroalkyl group may be linear, branched or cyclic. The $C_{1-10}$ fluoroalkyl group is preferably a $C_{1-4}$ fluoroalkyl group. An alkyl group all of which hydrogen atoms are substituted by fluorine atoms is also referred to as a perfluoroalkyl group.

The hydrogen atom on the $C_{6-14}$ aryl group may be substituted by a chlorine atom, a bromine atom, an iodine atom or a $C_{1-8}$ alkyl group.

The $C_{6-14}$ fluoroaryl group means an aryl group of which one or more hydrogen atoms are substituted by a fluorine atom or a $C_{1-4}$ fluoroalkyl group. It is preferred that all of the hydrogen atoms of the $C_{6-14}$ fluoroaryl group are substituted by fluorine atoms.

The $C_{4-14}$ heteroaryl group means an aromatic heterocyclic group having one or more nitrogen atoms, oxygen atoms or sulfur atoms. An example of the $C_{4-14}$ heteroaryl group includes a five-membered heteroaryl group such as pyrrolyl, imidazolyl, pyrazolyl, thienyl, furyl, oxazolyl, isoxazolyl, thiazolyl, isothiazolyl and thiadiazole; a six-membered heteroaryl group such as pyridinyl, pyrazinyl, pyrimidinyl and pyridazinyl; a condensed ring aromatic heterocyclic group such as indolyl, isoindolyl, quinolinyl, isoquinolinyl, benzofuranyl, isobenzofuranyl and chromenyl. The $C_{4-14}$ heteroaryl group is preferably a nitrogen atom-containing heterocyclic group and more preferably pyridinyl.

The $C_{4-14}$ fluoroheteroaryl group means a heteroaryl group of which one or more hydrogen atoms are substituted by a fluorine atom or a $C_{1-4}$ fluoroalkyl group.

The $C_{2-24}$ alkylpolyoxyalkylene group is preferably a group represented by the formula $-(Q^HO)_m R^H$ wherein $Q^H$ is $-CH_2-$, $-CH_2CH_2-$, $-CH_2CH_2CH_2-$, $-CH_2CH(CH_3)-$ or $-CH_2CH_2CH_2CH_2-$, $R^H$ is $-CH_3$ or $-CH_2CH_3$, and m is an integer of 1 or more and 20 or less. When "m" is 2 or more, $Q^H$ may be composed of one kind only or a plurality of kinds. When $Q^H$ is composed of a plurality of kinds, the arrangement of two or more $Q^H$ may be in a random state or a block state.

The $C_{2-24}$ fluoro(alkylpolyoxyalkylene) group means an alkylpolyoxyalkylene group of which one or more hydrogen atoms are substituted by a fluorine atom. A fluoro(alkylpolyoxyalkylene) group all of which hydrogen atoms are substituted by fluorine atoms is also referred to as a perfluoro(alkylpolyoxyalkylene) group.

The $C_{2-24}$ fluoro(alkylpolyoxyalkylene) group is preferably a group represented by the formula $-(Q^FO)_n R^F$ wherein $Q^F$ is $-CF_2-$, $-CF_2CF_2-$, $-CF_2CF_2CF_2-$, $-CF_2CF(CF_3)-$ or $-CF_2CF_2CF_2CF_2-$, $R^F$ is $-CF_3$ or $-CF_2CF_3$, and "n" is an integer of 1 or more and 20 or less. When "n" is 2 or more, $Q^F$ may be composed of one kind only or a plurality of kinds. When $Q^F$ is composed of a plurality of kinds, the arrangement of two or more $Q^F$ may be in a random state or a block state.

The $C_{2-6}$ fluoroalkylene group is an alkylene group of which one or more hydrogen atoms are substituted by a fluorine atom. The $C_{2-6}$ fluoroalkylene group may be linear, branched or cyclic. The $C_{2-6}$ fluoroalkyl group is preferably $-CF_2CF_2CF_2CF_2-$ or $-CF_2CF_2CF_2CF_2CF_2-$.

A specific example of the compound (i) includes $CF_3CH_2AH$, $CH_2FCH_2AH$, $CF_3CH_2AH$, $CF_3CF_2CH_2AH$, $(CF_3)_2CHAH$, $CF_3CH_2CH_2CH_2AH$, $CF_3CH_2CH(AH)CH_3$, $CF_3CHFCF_2CH_2AH$, $CF_3CF_2CF_2CH_2AH$, $(CF_3)_3CAH$, $CF_3CH_2CH_2CH_2CH_2AH$, $CF_3CF_2CH_2CH_2CH_2AH$, $CHF_2CF_2CH_2CH_2CH_2AH$, $CH_2FCH_2CH_2CH_2CH_2CH_2AH$, $CF_3CF_2CF_2CF_2CH_2CH_2AH$, $CF_3CF_2CF_2CF_2CF_2CH_2AH$, $CF_3CF_2CF_2CF_2CF_2CF_2CH_2CH_2AH$, $(CF_3)_3CCH(AH)CF_3$, $CF_3O(CF_2CF_2O)_nCH_2AH$, $CF_3O(CF_2CF(CF_3)O)_nCH_2AH$, $CF_3O(CF_2CF_2CF_2CF_2O)_nCF_2CF_2CF_2CH_2AH$, and the compounds represented by the following formulae wherein the symbols mean the same as defined above.

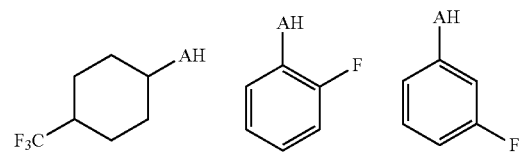

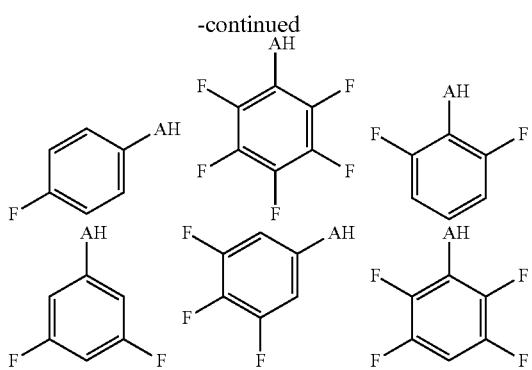

One kind of the compound (i) may be singly used, and alternatively two or more kinds of the compounds (i) may be used in combination. When two or more kinds of the compounds (i) are used in combination, an asymmetric fluorinated carbonate can be produced. It is however preferred to use one kind of the compound (i) in terms of the production efficiency or the like.

The compound (ii) is preferably a compound represented by the following formula (ii-1) and a compound represented by the following formula (ii-2) from the viewpoint that an acidity of the compounds is higher and the compounds are activated by the base more efficiently to obtain the target compound with high efficiency. The obtained fluorinated carbonate derivative is preferably a polymer containing the unit represented by the following formula (II-11) in the former case, and is preferably the compound represented by the following formula (II-21) or the following formula (II-22) in the latter case.

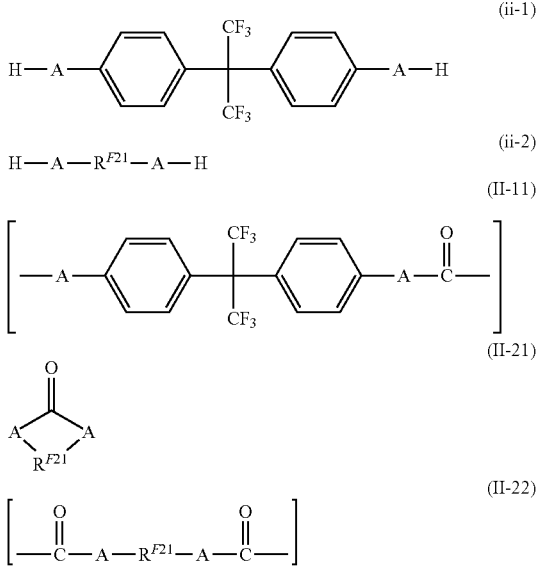

wherein "A" means the same as defined above, $R^{F21}$ is a $C_{3-10}$ fluoroalkylene group or a poly($C_{1-4}$ fluoroalkyleneoxy) group.

The $C_{3-10}$ fluoroalkylene group means a $C_{3-10}$ alkyl group of which one or more hydrogen atoms are substituted by a fluorine atom. The $C_{3-10}$ fluoroalkylene group may be linear, branched or cyclic.

It is preferred that the carbon number of the main chain of the $C_{3-10}$ fluoroalkylene group as $R^{F21}$ is 2 or 3 and the $C_{3-10}$ fluoroalkylene is a group which can form a stable cyclic structure such as a five-membered ring and a six-membered ring with a carbonate ester group (—O—C(=O)—O—), a carbonate dithioester group (—S—C(=O)—S—) or an urea group (—NH—C(=O)—NH—) from the viewpoint that the fluorinated cyclic carbonate can be obtained more efficiently. The $C_{3-10}$ fluoroalkylene group is more preferably a group represented by the formula —$CX^{21}X^{22}CX^{23}X^{24}$— wherein $X^{21}$, $X^{22}$, $X^{23}$ and $X^{24}$ are independently a hydrogen atom or a $C_{1-2}$ fluoroalkyl group, and one or more are a $C_{1-2}$ fluoroalkyl group, and particularly preferably —CH(CF$_3$)CH$_2$—, —CH(CF$_3$)CH(CF$_3$)— or —C(CF$_3$)$_2$C(CF$_3$)$_2$—.

The poly($C_{1-4}$ fluoroalkyleneoxy) group in the formula (ii-1) and the formula (II-22) is exemplified by a poly(fluoroethyleneoxy) and a poly(fluoropropyleneoxy). A polymerization degree of the poly($C_{1-4}$ fluoroalkyleneoxy) group is not particularly restricted, and may be 2 or more and 10 or less, and is preferably 5 or less. The number of the fluoro group as the substituent in the $C_{1-4}$ fluoroalkyleneoxy group may be 1 or more. The numbers of the fluoro groups as the substituent between the terminal part and the other part may be different from each other.

A specific example of the compound (ii-2) includes HACH(CF$_3$)CH$_2$AH, HACH(CF$_3$)CH(CF$_3$)AH, HACH$_2$CHFCH$_2$AH, HACH$_2$CF$_2$CF$_2$CH$_2$AH, HAC(CF$_3$)$_2$C(CF$_3$)$_2$AH and HACH$_2$CF$_2$CF$_2$CF$_2$CF$_2$CH$_2$AH.

A usage of the $C_{1-4}$ halogenated hydrocarbon and the fluorine-containing compound having the nucleophilic functional group is not particularly restricted, and one time by mole of the fluorine-containing compound having the nucleophilic functional group to the $C_{1-4}$ halogenated hydrocarbon may be used. A molar ratio of the fluorine-containing compound having the nucleophilic functional group to the $C_{1-4}$ halogenated hydrocarbon is preferably 0.001 or more and 1 or less in terms of the reaction efficiency and the reaction time. The molar ratio is more preferably 0.01 or more, even more preferably 0.1 or more, and more preferably 0.8 or less, even more preferably 0.5 or less. When the molar ratio is 1 or less, a reaction conversion rate of the fluorine-containing compound having the nucleophilic functional group becomes high so that a remained amount of the unreacted fluorine-containing compound having the nucleophilic functional group can be decreased. When the molar ratio is 0.001 or more, a halogenated carbonyl-like compound generated from the $C_{1-4}$ halogenated hydrocarbon is reacted with the fluorine-containing compound having the nucleophilic functional group more efficiently so that the halogenated carbonyl-like compound can be prevented from being discharged out of the reaction system more easily. In the case where the $C_{1-4}$ halogenated hydrocarbon is liquid under an ordinary temperature and an ordinary pressure so that the $C_{1-4}$ halogenated hydrocarbon can be used as a solvent, a ratio of the nucleophilic functional group-containing compound to the $C_{1-4}$ halogenated hydrocarbon may be adjusted to 1 mg/mL or more and 500 mg/mL or less.

The base usable in the present invention may be any one of an organic base and an inorganic base. Such an organic base is preferably an aliphatic linear tertiary amine, an aliphatic cyclic tertiary amine, a polycyclic tertiary amine and an aromatic heterocyclic amine, and particularly preferably an aromatic heterocyclic amine from the viewpoint that the fluorinated carbonate derivative can be obtained more efficiently. The reason why the fluorinated carbonate derivative can be obtained more efficiently by using an aromatic heterocyclic amine is not necessarily clear, and may be that an aromatic heterocyclic amine forms a complex salt by coordinating to the hydroxy group of the fluorine-containing compound so that the fluorine-containing compound having the hydroxy group becomes more activated.

The aromatic heterocyclic amine means an amine having an aromatic ring structure and a structure of which at least one carbon atom-hydrogen atom linkage forming the aromatic ring structure is substituted by a nitrogen atom.

A specific example of the organic base includes pyridine and the derivative thereof, such as pyridine, α-picoline, β-picoline, γ-picoline, 2,3-lutidine, 2,4-lutidine, 2,6-lutidine, 3,5-lutidine, 2-chloropyridine, 3-chloropyridine and 4-chloropyridine; an aliphatic linear tertiary amine such as trimethylamine, triethylamine, tributylamine and diisopropylethylamine; an aliphatic cyclic tertiary amine such as N-methylmorpholine, N-methylpyrrolidine and N-methylpiperidine; and a polycyclic tertiary amine such as 1,8-diazabicyclo[5.4.0]undec-7-ene and 1,4-diaza-bicyclo[2.2.2]octane.

A non-nucleophilic strong base may be used as the organic base. Such a non-nucleophilic strong base accelerates the reaction of the present invention due to the strong basicity thereof and may hardly decompose the halogenated carbonyl due to non-nucleophilicity. The "non-nucleophilic strong base" means a base of which nucleophilicity of the lone electron pair on the nitrogen atom is weak due to the steric hindrance and of which basicity ($pK_{BH+}$) in acetonitrile is 20 or more. An example of such a non-nucleophilic strong base includes 1,5,7-triazabicyclo[4.4.0]dec-5-ene (TBD, $pK_{BH+}$: 25.98), 7-methyl-1,5,7-triazabicyclo[4.4.0]dec-5-ene (MTBD, $pK_{BH+}$: 25.44), 1,8-diazabicyclo[5.4.0]undec-7-ene (DBU, $pK_{BH+}$: 24.33), 1,5-diazabicyclo[4.3.0]non-5-ene (DBN, $pK_{BH+}$: 23.89) and 1,1,3,3-tetramethylguanidine (TMG, $pK_{BH+}$: 23.30).

An example of the inorganic base includes an alkali metal hydroxide such as lithium hydroxide, sodium hydroxide and potassium hydroxide; an alkaline earth metal hydroxide such as calcium hydroxide; an alkali metal carbonate such as sodium carbonate and potassium carbonate; an alkaline earth metal carbonate such as calcium carbonate; and an alkali metal hydrogen carbonate such as sodium hydrogen carbonate.

The inorganic base may be micronized immediately before the use to be added to the reaction mixture, but an aqueous solution thereof is preferably added. A concentration of such an inorganic base aqueous solution may be appropriately adjusted and may be adjusted to 0.05 g/mL or more and 2 g/mL or less. The inorganic base aqueous solution is used for decomposing phosgene. Specifically, phosgene is decomposed into carbon dioxide and hydrogen chloride by the presence of water, and the generated hydrogen chloride can be neutralized by the inorganic base. It is remarkable that the present invention reaction proceeds even when the inorganic aqueous solution is used as Example described later, since the inventor considered that the reaction of the present invention proceeds by way of a halogenated carbonyl compound. In addition, the present invention reaction may possibly proceed without passing through a halogenated carbonyl, since the present invention reaction proceeds even when the inorganic aqueous solution is used.

Only one kind of the base may be singly used, and alternatively two or more kinds of the bases may be used in combination.

A ratio of the base to the fluorine-containing compound having the nucleophilic functional group is preferably 1.5 times or more by mole and 10 times or less by mole. The ratio is preferably 1.5 times or more by mole, more preferably 2.0 times or more by mole, particularly preferably 3.0 times or more by mole, and the most preferably 4.0 times or more by mole.

The present invention comprises the step of irradiating light on the composition containing the $C_{1-4}$ halogenated hydrocarbon, the fluorine-containing compound having the nucleophilic functional group and the base in the presence of oxygen.

An embodiment to mix the $C_{1-4}$ halogenated hydrocarbon, the fluorine-containing compound having the nucleophilic functional group and the base to obtain the composition is not particularly restricted. Total amount of each compound may be preliminarily mixed in a reaction vessel to obtain the composition, and the compounds may be added in several portions or continuously added at any speed to obtain the composition. When one of or both of the $C_{1-4}$ halogenated hydrocarbon and the fluorine-containing compound having the nucleophilic functional group are not liquid in an ordinary temperature and an ordinary pressure, a solvent which can appropriately dissolve the compounds and which does not inhibit the present invention reaction may be used. A specific example of such a solvent includes an aliphatic hydrocarbon solvent such as n-hexane; an aromatic hydrocarbon solvent such as benzene, toluene, xylene and chlorobenzene; an ether solvent such as diethyl ether, tetrahydrofuran and dioxane; and a nitrile solvent such as acetonitrile.

An example of an oxygen source includes air and purified oxygen gas. Purified oxygen gas may be used as a mixed gas with an inert gas such as nitrogen gas and argon gas. It is preferred to use air as an oxygen source in terms of cost and easiness of the production. An oxygen content in the oxygen source is preferably 15 vol % or more and 100 vol % or less in terms of high decomposition efficiency of the $C_{1-4}$ halogenated hydrocarbon into a halogenated carbonyl-like compound by light irradiation. The oxygen content may be appropriately determined depending on the kind of the $C_{1-4}$ halogenated hydrocarbon or the like. For example, when a $C_{1-4}$ chlorohydrocarbon compound such as dichloromethane, chloroform and tetrachloroethylene is used as the $C_{1-4}$ halogenated hydrocarbon, the oxygen content is preferably 15 vol % or more and 100 vol % or less. When a $C_{1-4}$ bromohydrocarbon compound such as dibromomethane and bromoform is used, the oxygen content is preferably 90 vol % or more and 100 vol % or less. Even when oxygen gas having an oxygen content of 100 vol % is used, the oxygen content may be adjusted to the above-described range by adjusting a flow rate of oxygen into the reaction system. A manner to supply a gas containing oxygen is not particularly restricted, and the gas may be supplied into the reaction system from an oxygen tank equipped with a flow rate adjustor or from an oxygen generating device.

The term "in the presence of oxygen" means any one of the state that the above-described each compound is contacted with oxygen and the state that there is oxygen in the above-described composition. The reaction of the present invention may be carried out under a stream of a gas containing oxygen but it is preferred to supply a gas containing oxygen into the composition by bubbling in terms of a high reaction yield.

An amount of oxygen-containing gas may be appropriately determined depending on the amount of the $C_{1-4}$ halogenated hydrocarbon or a shape of a reaction vessel. For example, an amount of the gas supplied to a reaction vessel per 1 minute to the $C_{1-4}$ halogenated hydrocarbon in the reaction vessel is preferably 5 times or more by volume. The amount is more preferably 25 times or more by volume, and even more preferably 50 times or more by volume. The upper limit of the amount is not particularly restricted, and the ratio is preferably 500 times or less by volume, more preferably 250 times or less by volume, and even more preferably 150 times or less by volume. The amount of oxygen supplied to a reaction vessel per 1 minute to the $C_{1-4}$ halogenated hydrocarbon in a reaction vessel is preferably 5 times or more by volume and 25 times or less by volume. When an amount of the gas is excessively large, the $C_{1-4}$ halogenated hydrocarbon may be possibly volatilized, but when the amount is excessively small, it may possibly become difficult to develop the reaction.

The light used for light irradiation is preferably a light containing a short wavelength light, more preferably a light containing ultraviolet light, and particularly preferably a light containing a light having a wavelength of 180 nm or more and 500 nm or less. A wavelength of the light may be appropriately determined depending on the kind of the $C_{1-4}$ halogenated hydrocarbon, and is more preferably 400 nm and even more preferably 300 nm or less. When the irradiated light contains a light of the above-described wavelength range, a halogenated carbonyl-like compound can be efficiently generated from the $C_{1-4}$ halogenated hydrocarbon.

A specific example of a light source for the light irradiation includes sunlight, low pressure mercury lamp, medium pressure mercury lamp, high pressure mercury lamp, ultrahigh pressure mercury lamp, chemical lamp, black light lamp, metal halide lamp and LED lamp. A low pressure mercury lamp is preferably used in terms of a reaction efficiency and a cost.

A strength of the irradiation light is preferably 10 $\mu W/cm^2$ or more and 500 $\mu W/cm^2$ or less. The irradiation light strength is more preferably 100 $\mu W/cm^2$ or less, and particularly preferably 40 $\mu W/cm^2$ or less. An irradiation time is preferably 0.5 hours or more and 10 hours or less, more preferably 1 hour or more and 6 hours or less, and even more preferably 2 hours or more and 4 hours or less.

As an embodiment to irradiate light, for example, the light may be continuously irradiated from the reaction initiation to the reaction completion, irradiation and unirradiation of the light may be alternately repeated, and the light may be irradiated from the reaction initiation for a predetermined time only. It is preferred to continuously irradiate light from the reaction initiation to the reaction completion.

A temperature during the reaction may be adjusted to 0° C. or higher and 50° C. or lower. The temperature is more preferably 10° C. or higher, particularly preferably 20° C. or higher, and more preferably 40° C. or lower, particularly preferably 30° C. or lower.

A reaction apparatus usable in the production method of the present invention is exemplified by a reaction vessel equipped with a light irradiation means. A reaction apparatus may be equipped with a stirring device and a temperature control means. One embodiment of a reaction apparatus usable in the production method of the present invention is shown as FIG. 1. The reaction apparatus shown as FIG. 1 has a light irradiation means 1 in a tubular reaction vessel 6. The above-described raw material compounds are added into a tubular reaction vessel 6, and light is irradiated by using a light irradiation means 1 while a gas containing oxygen is supplied into the tubular reaction vessel 6 or a gas containing oxygen is blown into the composition to cause bubbling (not shown in the FIGURE) for the reaction. When a light irradiation means 1 is covered with a jacket 2 or the like, it is preferred that the jacket is composed of a material through which the short wavelength light penetrates. A light may be irradiated from outside a reaction vessel. In such a case, the reaction vessel is composed of a material through which the short wavelength light penetrates. An example of a material through which the short wavelength light penetrates includes quartz glass.

The product obtained by the reaction may be further purified by a method such as distillation, removal of raw material compounds under reduced pressure, column chromatography, liquid separation, extraction, washing and recrystallization.

When the hydroxy group-containing compound, thiol group-containing compound or amino group-containing compound is used as the raw material fluorine-containing compound having the nucleophilic functional group, a carbonate derivative respectively having a carbonate ester group (—O—C(=O)—O—), a carbonate dithioester group (—S—C(=O)—S—) or a urea group (—NH—C(=O)—NH—) is obtained. When the hydroxy group-containing compound and the amino group-containing compound are used in combination, a carbonate derivative having a urethane group (—O—C(=O)—NH—) is obtained. When the thiol group-containing compound and the amino group-containing compound are used in combination, a carbonate derivative having a thiourethane group (—S—C(=O)—NH—) is obtained.

The fluorinated carbonate derivative produced by the present invention method is useful as an electrolyte solvent of a lithium-ion secondary battery. The fluorinated carbonate such as a bis(hexafluoroisopropyl) carbonate is useful as an alternate phosgene which is highly reactive and which is easy to be handled. The fluorinated polycarbonate produced by the present invention method is excellent in chemical resistance and is useful as an engineering plastic.

The present application claims the benefit of the priority date of Japanese patent application No. 2017-97682 filed on May 16, 2017. All of the contents of the Japanese patent application No. 2017-97682 filed on May 16, 2017, are incorporated by reference herein.

EXAMPLES

Hereinafter, the present invention is described in more detail with Examples. The present invention is however not restricted to the following Examples in any way, and it is possible to work the present invention according to the Examples with an additional appropriate change within the range of the above descriptions and the following descriptions. Such a changed embodiment is also included in the technical scope of the present invention. The yield of the target compound was calculated on the basis of the amount of the used compound having a hydroxy group.

Example 1: Synthesis of bis(2,2,2-trifluoroethyl) carbonate

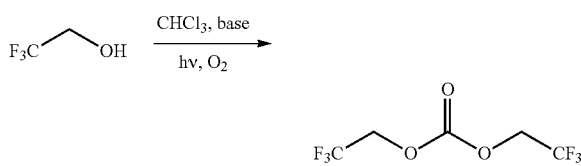

A quartz glass jacket having a diameter of 30 mm was inserted into a tubular reaction vessel having a diameter of 42 mm and a volume of 100 mL, and a low pressure mercury lamp ("UVL20PH-6" manufactured by SEN Light, 20 W, φ24×120 mm) was further inserted into the quartz glass jacket to construct a reaction system. A schematic picture of the reaction system is shown as FIG. 1. In the reaction vessel, purified chloroform (20 mL), 2,2,2-trifluoroethanol (0.718 mL, 10 mmol) and 5 times by mole of pyridine (4.03 mL) to the 2,2,2-trifluoroethanol were added. The mixture was stirred to be mixed. Oxygen gas was blown into the stirred reaction mixture at a flow rate of 0.5 L/min at 20° C. to cause bubbling, and a light was irradiated from the low pressure mercury lamp. After 2 hours, the reaction mixture was washed with water and the organic phase was dried by using anhydrous sodium sulfate. The organic phase was analyzed by $^1$H-NMR and $^{19}$F-NMR; as a result, it was confirmed that bis(2,2,2-trifluoroethyl) carbonate was generated as the target compound with the yield of 98%.

Example 2: Synthesis of bis(3,3,3-trifluoropropyl) carbonate

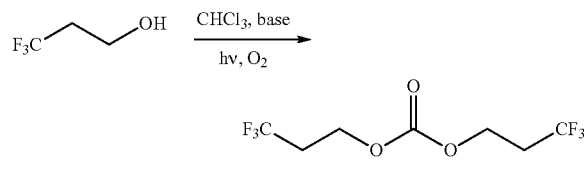

The reaction was carried out similarly to the above-described Example 1 except that 3,3,3-trifluoropropanol (0.220 mL, 2.5 mmol) was used instead of 2,2,2-trifluoroethanol and the reaction time changed to 1.5 hours. Dichloromethane and water were added to the reaction mixture after the reaction, and the aqueous phase and the organic phase were separated. The organic phase was dried by using anhydrous sodium sulfate and then concentrated under reduced pressure to obtain yellow liquid. The yellow liquid was analyzed by $^1$H-NMR and $^{19}$F-NMR; as a result, it was confirmed that bis(3,3,3-trifluoropropyl) carbonate was generated as the target compound with the yield of 96%.

Example 3: Synthesis of bis(hexafluoroisopropyl) carbonate

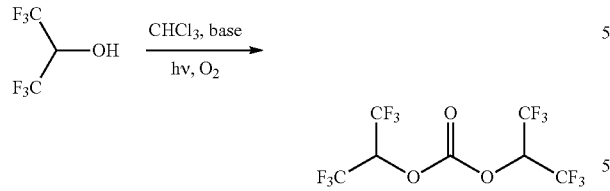

(1) Use of Pyridine as Organic Base

The reaction was carried out similarly to the above-described Example 1 except that hexafluoroisopropanol (1.04 mL, 10 mmol) was used instead of 2,2,2-trifluoroethanol and the usage of pyridine was changed to 3.5 times by mole to the hexafluoroisopropanol. The reaction mixture was analyzed by $^1$H-NMR and $^{19}$F-NMR; as a result, it was confirmed that bis(hexafluoroisopropyl) carbonate was generated as the target compound with the yield of 70%. At the completion of the reaction, the reaction mixture was separated into an upper layer containing a pyridine hydrochloride salt and a lower layer as a chloroform solution of the target compound.

(2) Use of Triethylamine as Organic Base

The reaction was carried out similarly to the above-described Example 3(1) except that 3.5 times by mole of triethylamine (4.9 mL) to the hexafluoroisopropanol was used as an organic base instead of pyridine and the reaction time was set to 3 hours. The reaction mixture was concentrated under reduced pressure after the reaction. The distilled fraction was captured by using liquid nitrogen to be analyzed by $^1$H-NMR and $^{19}$F-NMR; as a result, it was confirmed that bis(hexafluoroisopropyl) carbonate was generated as the target compound with the yield of about 20%. The yield might be decreased due to the decomposition of triethylamine during the reaction and the generation of a formate ester as a by-product.

(3) Use of 2,6-lutidine as Organic Base

The reaction was carried out similarly to the above-described Example 3(1) except that 3.5 times by mole of 2,6-lutidine (4.05 mL) to the hexafluoroisopropanol was used as an organic base instead of pyridine and the reaction time was set to 0.5 hours. The reaction mixture was directly analyzed by $^1$H-NMR and $^{19}$F-NMR; as a result, it was confirmed that bis(hexafluoroisopropyl) carbonate was generated as the target compound with the yield of about 50%. The reason why the raw material remained and the yield was relatively decreased may be that the basicity of 2,6-lutidine is stronger than pyridine and the ability thereof to form a hydrochloride salt with the generated HCl is strong. At the completion of the reaction, the reaction mixture was separated into two layers similarly to the above-described Example 3(1).

Comparative Example 1: Synthesis of Hexafluoroisopropyl Carbonate

The reaction was carried out similarly to the above-described Example 3(1) except that an organic base was not used and the reaction time was set to 3 hours, but hexafluoroisopropyl carbonate as the target compound was not generated at all.

Example 4: Synthesis of bis(nonafluoro-t-butyl) carbonate

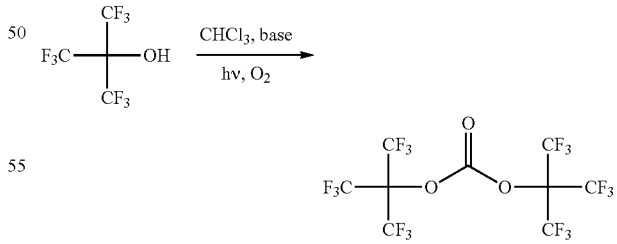

(1) Use of Pyridine as Organic Base

Purified chloroform (20 mL), nonafluoro-t-butanol (0.694 g, 5 mmol) and 5 times by mole of pyridine (2 mL) to the nonafluoro-t-butanol were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 1 hour, the reaction mixture was directly analyzed by $^{19}$F-NMR; as a result, it was confirmed that bis(nonafluoro-t-butyl) carbonate was generated as the target compound with the yield of 22%.

(2) Use of 2,6-lutidine as Organic Base

It was confirmed that bis(nonafluoro-t-butyl) carbonate was generated as the target compound with the yield of 35% similarly to the above-described Example 4(1) except that 5 times by mole of 2,6-lutidine (2.9 mL) to the nonafluoro-t-butanol was used as an organic base instead of pyridine.

Example 5: Synthesis of bis(pentafluorophenyl) carbonate

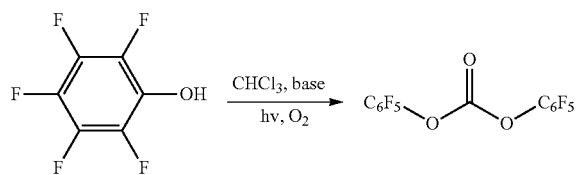

Purified chloroform (20 mL), pentafluorophenol (2.28 g, 10 mmol) and 3.5 times by mole of pyridine (2.82 mL) to the pentafluorophenol were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 2 hours, the reaction mixture was washed with water, the organic phase was dried by anhydrous sodium sulfate, and then chloroform was distilled away under reduced pressure. The thus obtained residue was analyzed by $^1$H-NMR; as a result, it was confirmed that bis(pentafluorophenyl) carbonate was generated as the target compound with the yield of 63%.

Example 6: Synthesis of 4,4'-(hexafluoroisopropylidene)bisphenol polycarbonate

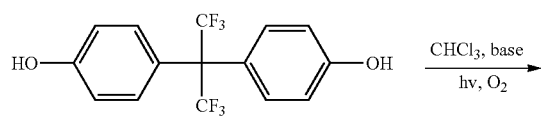

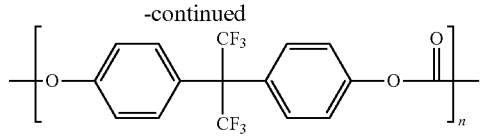

Purified chloroform (30 mL), 2,2-bis(4-hydroxyphenyl) hexafluoropropane (1.68 g, 5 mmol) and 5 times by mole of pyridine (2 mL) to the 2,2-bis(4-hydroxyphenyl)hexafluoropropane were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 2 hours, methanol (30 mL) was added to the reaction mixture. The solid content was washed with methanol and dried in vacuo to obtain a white solid. The white solid was analyzed by $^1$H-NMR and $^{19}$F-NMR; as a result, it was confirmed that 4,4'-(hexafluoroisopropylidene)bisphenol polycarbonate was generated as the target compound with the yield of more than 99%.

The obtained 4,4'-(hexafluoroisopropylidene)bisphenol polycarbonate was analyzed by gel permeation chromatography (GPC) in the following condition to determine the molecular weight. The result is shown in Table 1.

Device: High Performance GPC Device ("HLC-8320GPC" manufactured by Tosoh Corporation)
Column: Column for Super High Molecule ("TSKgel GMHHR-H×2" manufactured by Tosoh Corporation)

Moving phase: chloroform
Flow rate: 1.0 mL/min
Oven temperature: 40° C.
Concentration: 0.3 w/v %
Injected amount: 100 µL
Molecular weight standard: polystyrene
Detector: RI

TABLE 1

| Mn | Mw | Mw/Mn |
|---|---|---|
| 6,400 | 14,000 | 2.2 |

As the result shown in Table 1, it was found that the fluorinated polycarbonate ester synthesized by the present invention method has sufficiently high molecular weight, and the molecular weight distribution is relatively narrow.

Example 7: Photoinduced Copolymerization of Bisphenol A and 4',4'-(hexafluoroisopropylidene)diani-line

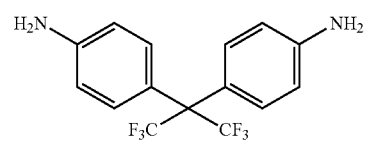

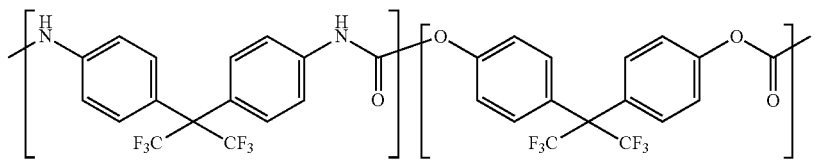

Purified chloroform (30 mL), 2,2-bis(4-aminophenyl) hexafluoropropane (0.57 g, 2.5 mmol), 2,2-bis(4-hydroxyphenyl)propane (0.84 g, 2.5 mmol) and sodium hydroxide aqueous solution (NaOH: 100 mmol, 20 mL) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 3 hours, dichloromethane and water were added to the reaction mixture and the precipitate was obtained by filtration with suction. The obtained precipitate was washed with methanol and then dried in vacuo to obtain a light brown solid (yield: 35%). The light brown solid was analyzed by $^1$H-NMR and $^{19}$F-NMR; as a result, it was confirmed that the target compound was generated.

Example 8: Synthesis of bis(hexafluoroisopropyl) carbonate

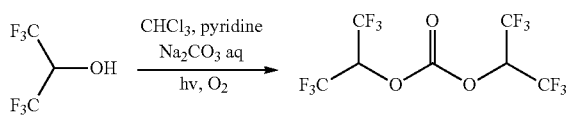 [SMILES: OC(C(F)(F)F)C(F)(F)F ; O=C(OC(C(F)(F)F)C(F)(F)F)OC(C(F)(F)F)C(F)(F)F]

Purified chloroform (30 mL), 1,1,1,3,3,3-hexafluoro-2-propanol (10 mmol), pyridine (0.8 mL, 10 mmol) and sodium carbonate aqueous solution (Na$_2$CO$_3$: 5.3 g, 50 mmol, 20 mL) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 2 hours, dichloromethane and water were added to the reaction mixture and the organic phase and the aqueous phase were separated. The organic phase was dried by anhydrous sodium sulfate and was analyzed by $^1$H-NMR and $^{19}$F-NMR; as a result, it was confirmed that the target compound was generated with the yield of 6%.

Example 9: Synthesis of bis(4-fluorophenyl) carbonate

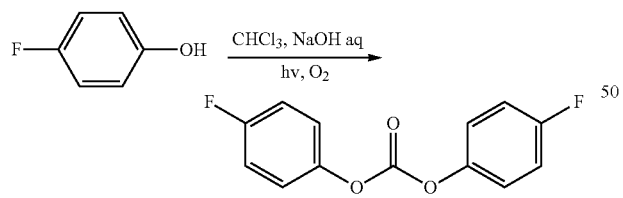

Purified chloroform (30 mL), 4-fluorophenol (1.12 g, 10 mmol) and sodium hydroxide aqueous solution (NaOH: 100 mmol, 20 mL) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp. After 3 hours, dichloromethane and water were added to the reaction mixture and the organic phase and the aqueous phase were separated. The organic phase was dried by anhydrous sodium sulfate, concentrated under reduced pressure and dried under reduced pressure at 60° C. to obtain a white powder (yield: 37%). The white powder was analyzed by $^1$H-NMR, $^{19}$F-NMR IR and mass spectrum to confirm that the target compound was generated.

Example 10: Synthesis of bis(3,5-difluorophenyl) carbonate

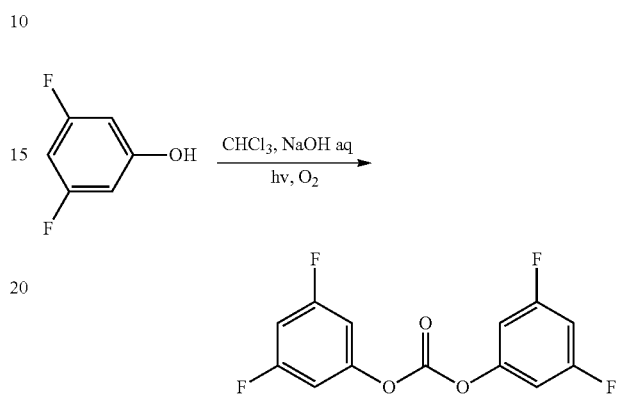

A brown powder was obtained (yield: 80%) similarly to the above-described Example 8 except that 3,5-difluorophenol (1.33 g, 10 mmol) was used instead of 4-fluorophenol, hexane was used instead of dichloromethane after the reaction, the generated precipitate was dissolved in acetone, and the solution was dried with anhydrous sodium sulfate and then concentrated under reduced pressure. The brown powder was analyzed by $^1$H-NMR, $^{19}$F-NMR IR and mass spectrum to confirm that the target compound was generated.

Example 11: Synthesis of bis(2,6-difluorophenyl) carbonate

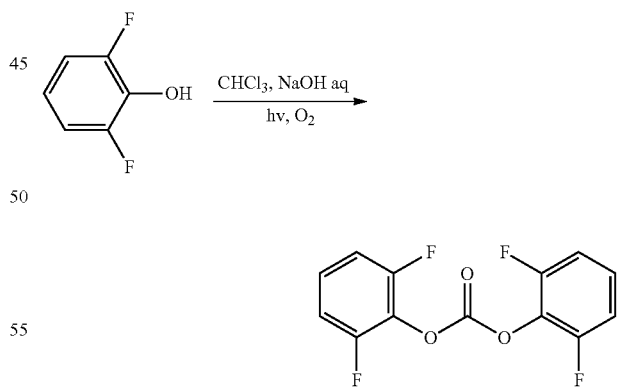

A brown powder was obtained (yield: 24%) similarly to the above-described Example 8 except that 2,6-difluorophenol (1.33 g, 10 mmol) was used instead of 4-fluorophenol, and the organic phase after the reaction was washed with water 4 times and dried with anhydrous sodium sulfate. The brown powder was analyzed by $^1$H-NMR, $^{19}$F-NMR IR and mass spectrum to confirm that the target compound was generated.

Example 12: Synthesis of bis(3,4,5-trifluorophenyl) carbonate

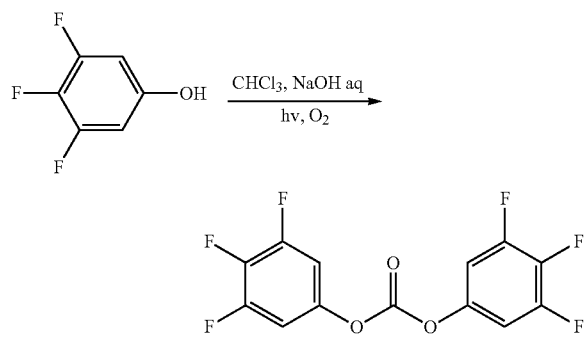

A white powder was obtained (yield: 87%) similarly to the above-described Example 8 except that 3,4,5-trifluorophenol (1.46 g, 10 mmol) was used instead of 4-fluorophenol, the organic phase after the reaction was concentrated under reduced pressure, and the thus obtained residue was washed with hexane and dried under reduced pressure at 60° C. The white powder was analyzed by $^1$H-NMR, $^{19}$F-NMR IR and mass spectrum to confirm that the target compound was generated.

Example 13: Synthesis of bis(2,3,5,6-tetrafluorophenyl) carbonate

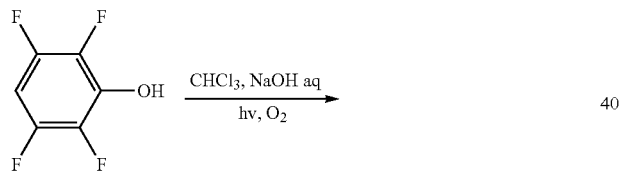

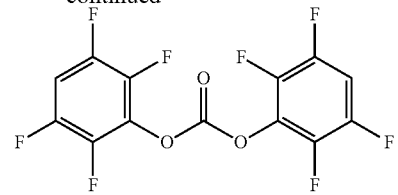

An oil was obtained (yield: 28%) similarly to the above-described Example 8 except that 2,3,5,6-tetrafluorophenol (1.66 g, 10 mmol) was used instead of 4-fluorophenol and distillation was carried out after the reaction by using Kugel Rohr at 70 to 80° C. The oil was analyzed by $^1$H-NMR, $^{19}$F-NMR IR and mass spectrum to confirm that the target compound was generated.

Example 14: Synthesis of bis(pentafluorophenyl) carbonate

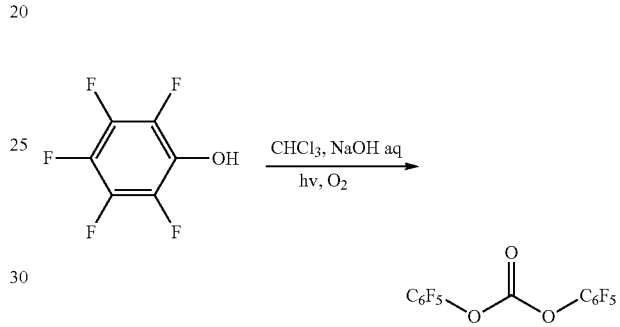

A yellow powder was obtained (yield: 55%) similarly to the above-described Example 8 except that pentafluorophenol (1.84 g, 10 mmol) was used instead of 4-fluorophenol and distillation was carried out by using Kugel Rohr at 110 to 170° C. The yellow powder was analyzed by 1H-NMR, $^{19}$F-NMR IR and mass spectrum to confirm that the target compound was generated.

Example 15: Photoinduced Copolymerization of Bisphenol AF and 4',4'-(hexafluoroisopropylidene) dianiline

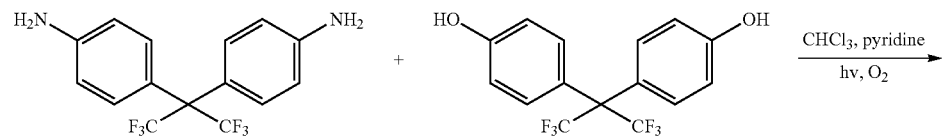

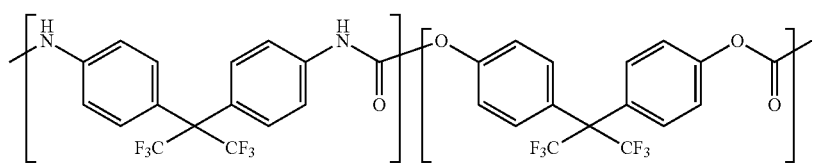

Purified chloroform (20 mL), 2,2-bis(4-aminophenyl) hexafluoropropane (0.862 g, 2.5 mmol), 2,2-bis(4-hydroxyphenyl)hexafluoropropane (0.824 g, 2.5 mmol) and pyridine (4.03 mL, 50 mmol) were added to the above-described reaction vessel, and the mixture was stirred to be mixed. Oxygen gas was blown into the stirred reaction mixture at a flow rate of 0.5 L/min at 40° C. to cause bubbling, and a light was irradiated from the low pressure mercury lamp for 1 hour. Further, after stopping the irradiation, the temperature of the reaction mixture was increased to 50° C. and the reaction was carried out for 15 minutes. After the reaction, methanol was added to the reaction mixture. The solid content was washed with methanol and dried in vacuo at 80° C. to obtain an orange powder (yield: 56%). The powder was analyzed by $^1$H-NMR, $^{19}$F-NMR and IR to confirm that the target compound was generated.

The molecular weight of the obtained copolymer was determined similarly to the above-described Example 6. The result is shown in Table 2.

TABLE 2

| Mn | Mw | Mw/Mn |
|---|---|---|
| 7,100 | 16,000 | 2.3 |

As the result shown in Table 2, it was found that the fluorinated polyurethan synthesized by the present invention method has sufficiently high molecular weight, and the molecular weight distribution is relatively narrow.

Example 16: Carbonating Reaction of 1H,1H,8H,8H-perfluoro-3,6-dioxaoctane-1,8-diol

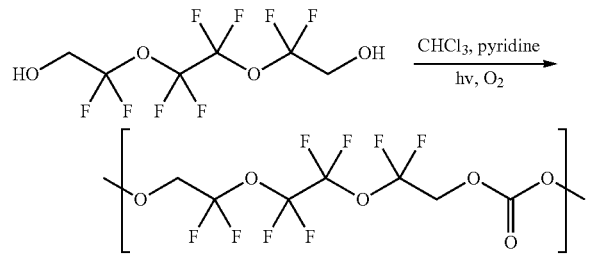

Purified chloroform (20 mL), 1H,1H,8H,8H-perfluoro-3,6-dioxaoctane-1,8-diol (1.47 g, 5 mmol) and pyridine (4.03 mL, 50 mmol) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp for 1 hour. Then, water was added to the reaction mixture and the precipitate was obtained by filtration. The obtained precipitate was dissolved in acetone. The solution was separated into two layers. The lower layer was separated from the upper layer. The lower layer was dried in vacuo at 60° C. to obtain a yellow oil (yield: 54%). The oil was analyzed by $^1$H-NMR and $^{19}$F-NMR to confirm that the target compound was generated.

Example 17: Carbonating Reaction of 1H,1H,10H,10H-hexadecafluoro-1,10-decanediol

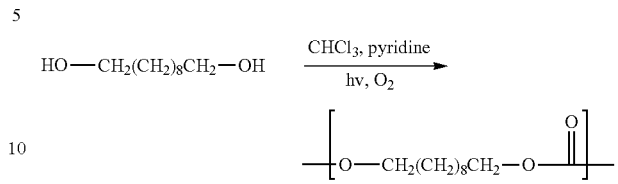

Purified chloroform (20 mL), 1H,1H,10H,10H-hexadecafluoro-1,10-decanediol (2.39 g, 2.5 mmol) and pyridine (4.03 mL, 50 mmol) were added to the above-described reaction vessel, and the mixture was stirred to be mixed. Oxygen gas was blown into the stirred reaction mixture at a flow rate of 0.5 L/min at 30° C. to cause bubbling, and a light was irradiated from the low pressure mercury lamp for 2 hours. Then, water was added to the reaction mixture and the precipitate was obtained by filtration. The obtained precipitate was washed with methanol (40 ml) to obtain a white powder (yield: 48%). The powder was analyzed by $^1$H-NMR, $^{19}$F-NMR and IR to confirm that the target compound was generated.

Example 18: Synthesis of 1,3-bis(pentafluorophenyl)urea

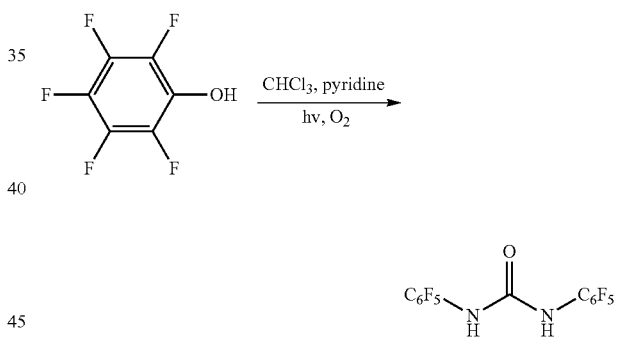

Purified chloroform (20 mL), pentafluoroaniline (10 mmol) and pyridine (50 mmol) were added to the above-described reaction vessel, and the mixture was stirred to be mixed. Oxygen gas was blown into the stirred reaction mixture at a flow rate of 0.5 L/min at 40° C. to cause bubbling, and a light was irradiated from the low pressure mercury lamp for 2 hours. Then, water and dichloromethane were added to the reaction mixture, and the organic phase and the aqueous phase were separated. The organic phase was dried with anhydrous sodium sulfate and concentrated under reduced pressure. Dichloromethane and hexane were added to the obtained residue, and the generated precipitate was obtained by suction filtration. The precipitate was subjected to silica gel column chromatography (eluent: ethyl acetate) and recrystallized by using ethyl acetate and hexane to obtain a light brown crystal (amount: 0.31 g, yield: 16%). The crystal was analyzed by $^1$H-NMR, $^{19}$F-NMR, IR and mass spectrum to confirm that the target compound was generated.

Example 19: Reaction to Obtain Polyurea from 4',4'-(hexafluoroisopropylidene)dianiline Purified chloroform (20 mL), 4',4'-(hexafluoroisopropylidene)dianiline (1.725 g, 5 mmol) and pyridine (4.03 mL, 50 mmol) were added to the above-described reaction vessel, and the mixture was stirred to be mixed. Oxygen gas was blown into the stirred reaction mixture at a flow rate of 0.5 L/min at 20° C. to cause bubbling, and a light was irradiated from the low pressure mercury lamp for 1 hour. Then, methanol was added to the reaction mixture, and the mixture was maintained at 70° C. for 1 hour. Water was added to the mixture, and the generated precipitate was obtained by filtration. The precipitate was washed with methanol and dried in vacuo to obtain an orange powder (yield: 44%). The powder was analyzed by $^1$H-NMR, $^{19}$F-NMR and IR to confirm that the target compound was generated.

EXPLANATION OF REFERENCES

1: Light-irradiating means, 2: Jacket, 3: Water bath, 4: Stirring bar, 5: Heating medium or Cooling medium, 6: Tubular reaction vessel

The invention claimed is:

1. A method for producing a fluorinated carbonate derivative, the method comprising
   irradiating light on a composition containing a $C_{1-4}$ halogenated hydrocarbon having one or more kinds of halogen atoms selected from the group consisting of a chlorine atom, a bromine atom and an iodine atom, a fluorine-containing compound having a nucleophilic functional group and a base in the presence of oxygen,
   wherein the fluorine-containing compound is a compound represented by formula (i) and the fluorinated carbonate derivative is a fluorinated carbonate derivative represented by formula (I), or
   the fluorine-containing compound is a compound represented by formula (ii) and the fluorinated carbonate derivative is a fluorinated polycarbonate derivative containing a unit represented by formula (II-1) or a fluorinated cyclic carbonate derivative represented by formula (II-2):

$R^{F1}$-A-H  (i)

H-A-$R^{F2}$-A-H  (ii)

$R^{F1}$-A-C(=O)-A-$R^{F1}$  (I)

[-A-$R^{F2}$-A-C(=O)-]  (II-1)

(II-2) [cyclic carbonate structure with A, A, C=O and $R^{F2}$]

wherein
A is O, S or NH,
$R^{F1}$ is an unreactive fluorine atom-containing monovalent organic group, and
$R^{F2}$ is an unreactive fluorine atom-containing divalent organic group.

2. The method according to claim 1, wherein the fluorine-containing compound is a compound represented by formula (i-1) and the fluorinated carbonate derivative is a fluorinated carbonate derivative represented by formula (I-1), the fluorine-containing compound is a compound represented by formula (i-2) and the fluorinated carbonate derivative is a fluorinated carbonate derivative represented by formula (I-2), or the fluorine-containing compound is a compound represented by formula (i-3) and the fluorinated carbonate derivative is a fluorinated carbonate derivative represented by formula (I-3):

$R^{F11}CH_2$-A-H  (i-1)

$(R^{F12})_2$CH-A-H  (i-2)

$(R^{F13})_3$C-A-H  (i-3)

$R^{F11}CH_2$-A-C(=O)-A-$CH_2$—$R^{F11}$  (I-1)

$(R^{F12})_2$CH-A-C(=O)-A-CH$(R^{F12})_2$  (I-2)

$(R^{F13})_3$C-A-C(=O)-A-C$(R^{F13})_3$  (I-3)

wherein
A is O, S or NH,
$R^{F11}$ is a $C_{1-10}$ fluoroalkyl group, a $C_{6-14}$ fluoroaryl group, a $C_{4-14}$ fluoroheteroaryl group or a $C_{2-24}$ fluoro(alkylpolyoxyalkylene) group,
two $R^{F12}$ are independently a $C_{1-10}$ alkyl group, a $C_{1-10}$ fluoroalkyl group, a $C_{6-14}$ aryl group, a $C_{6-14}$ fluoroaryl group, a $C_{4-14}$ heteroaryl group, a $C_{4-14}$ fluoroheteroaryl group, a $C_{2-24}$ alkylpolyoxyalkylene group or a $C_{2-24}$ fluoro(alkylpolyoxyalkylene) group, and one or two $R^{F12}$ are a $C_{1-10}$ fluoroalkyl group, a $C_{6-14}$ fluoroaryl group, a $C_{4-14}$ fluoroheteroaryl group or a $C_{2-24}$ fluoro(alkylpolyoxyalkylene) group, or two $R^{F12}$ cooperatively form a $C_{2-6}$ fluoroalkylene group or a 1,2-fluoroarylene group, and
three $R^{F13}$ are independently a $C_{1-10}$ alkyl group, a $C_{1-10}$ fluoroalkyl group, a $C_{6-14}$ aryl group, a $C_{6-14}$ fluoroaryl group, a $C_{4-14}$ heteroaryl group, a $C_{4-14}$ fluoroheteroaryl group, a $C_{2-24}$ alkylpolyoxyalkylene group or a $C_{2-24}$ fluoro(alkylpolyoxyalkylene) group, and one, two or three $R^{F13}$ are a $C_{1-10}$ fluoroalkyl group, a $C_{6-14}$ fluoroaryl group, a $C_{4-14}$ fluoroheteroaryl group or a $C_{2-24}$ fluoro(alkylpolyoxyalkylene) group.

3. The method according to claim 1, wherein the fluorine-containing compound is a compound represented by formula (ii-1) and the fluorinated carbonate derivative is a fluorinated polycarbonate derivative represented by formula (II-11), or the fluorine-containing compound is a compound represented by formula (ii-2) and the fluorinated carbonate derivative is a fluorinated cyclic carbonate derivative represented by formula (II-21) or a fluorinated linear carbonate derivative represented by formula (II-22):

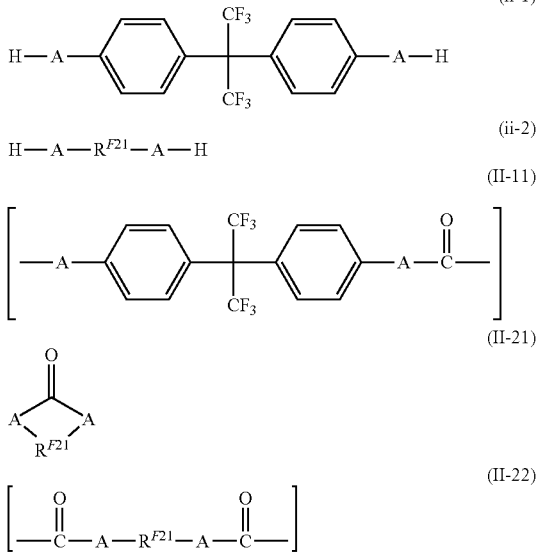

wherein

A is O, S or NH, and $R^{F21}$ is a $C_{3-10}$ fluoroalkylene group or a poly($C_{1-4}$ fluoroalkyleneoxy) group.

4. The method according to claim 1, wherein the $C_{1-4}$ halogenated hydrocarbon is a $C_{1-4}$ polyhalogenated hydrocarbon.

5. The method according to claim 1, wherein the $C_{1-4}$ halogenated hydrocarbon is chloroform.

6. The method according to claim 1, wherein the base is one or more bases selected from the group consisting of a heterocyclic aromatic amine, a non-nucleophilic strong base and an inorganic base.

7. The method according to claim 6, wherein the base comprises a heterocyclic aromatic amine, which is pyridine, picoline or lutidine.

8. The method according to claim 6, wherein the base comprises a non-nucleophilic strong base, which is 1,5,7-triazabicyclo[4.4.0]dec-5-ene, 7-methyl-1,5,7-triazabicyclo[4.4.0]dec-5-ene, 1,8-diazabicyclo[5.4.0]undec-7-ene, 1,5-diazabicyclo[4.3.0]non-5-ene or 1,1,3,3-tetramethylguanidine.

9. The method according to claim 6, wherein the base comprises an inorganic base, which is an alkali metal hydroxide, an alkali metal hydrogen carbonate or an alkali metal carbonate.

10. The method according to claim 1, wherein a molar ratio of the fluorine-containing compound to the $C_{1-4}$ halogenated hydrocarbon ranges from 0.001 to 1.

11. The method according to claim 1, wherein a molar ratio of the base to the fluorine-containing compound ranges from 1.5 to 10.

12. The method according to claim 1 wherein a wavelength of the light irradiated on the composition is 180 nm or more and 500 nm or less.

* * * * *